Figure 1:
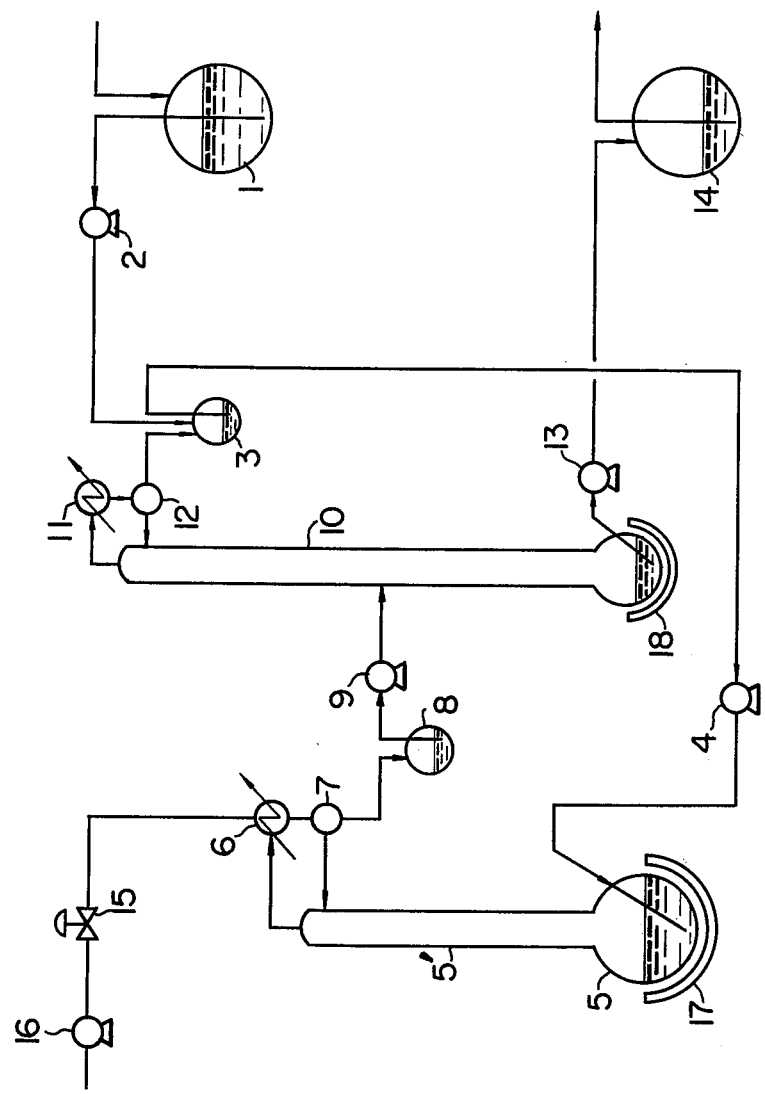

United States Patent [19]
Hirakawa et al.

[11] 4,197,251
[45] Apr. 8, 1980

[54] PROCESS FOR PRODUCING OCTAMETHYLCYCLOTETRASILOXANE

[75] Inventors: Keizo Hirakawa; Makoto Honda, both of Tokyo, Japan

[73] Assignee: Asahi Kasei Kogyo Kabushiki Kaisha, Osaka, Japan

[21] Appl. No.: 17,260

[22] Filed: Mar. 5, 1979

[30] Foreign Application Priority Data

Mar. 6, 1978 [JP] Japan ................................. 53-24478

[51] Int. Cl.$^2$ .............................................. C07F 7/08
[52] U.S. Cl. ................................................. 556/460
[58] Field of Search ................................. 260/448.2 E

[56] References Cited

U.S. PATENT DOCUMENTS 3,842,110  10/1974  Razzano .................. 260/448.2 E
3,989,733  11/1976  Okamoto et al. ......... 260/448.2 E

FOREIGN PATENT DOCUMENTS 33-2149  4/1958  Japan .
843273   8/1960  United Kingdom .

Primary Examiner—Paul F. Shaver
Attorney, Agent, or Firm—Armstrong, Nikaido, Marmelstein & Kubovcik

[57] ABSTRACT

Octamethylcyclotetrasiloxane can be produced from dimethylsiloxane effectively by suppressing the by-production of undesirable other siloxanes by reacting dimethylsiloxane in the presence of an alkaline catalyst, an inert solvent and recycled by-produced cyclic dimethylsiloxanes containing at least hexamethylcyclotrisiloxane in a reactor, while distilling volatile cyclic dimethylsiloxanes produced, said recycled by-produced cyclic dimethylsiloxanes containing at least hexamethylcyclotrisiloxane having been separated from the volatile cyclic dimethylsiloxanes by recovering octamethylcyclotetrasiloxane and recycled to the reactor.

14 Claims, 3 Drawing Figures

PROCESS FOR PRODUCING OCTAMETHYLCYCLOTETRASILOXANE

This invention relates to a process for producing octamethylcyclotetrasiloxane.

It is well known that octamethylcyclotetrasiloxane [(CH$_3$)$_2$SiO]$_4$ is useful as a general purpose starting material for producing viscous dimethylpolysiloxane oils, dimethylpolysiloxane gums and the like that are suitable for conversion to silicone elastomers. Recently, demands for properties of silicones become higher and higher. In order to obtain silicones satisfying these demands, control of the reaction rate, control of the molecular weight distribution, and the like become necessary more and more, and thus a demand for octamethylcyclotetrasiloxane as a starting material having high purity becomes greater.

On the other hand, various methods for producing cyclic diorganosiloxanes such as octamethylcyclotetrasiloxane and the like have been proposed. For example, British Pat. No. 843,273 discloses a process for producing pure low molecular cyclic dimethylsiloxanes suitable as a starting material for dimethylpolysiloxane oils and dimethylpolysiloxane gums, which can produce silicone elastomers. This process is an excellent one for producing cyclic dimethylsiloxanes containing substantially no monomethylsiloxane group and no trimethylsiloxane group using a hydrolyzate of dimethyldichlorosilane of industrial grade as a starting material but by-production of hexamethylcyclotrisiloxane [(CH$_3$)$_2$SiO]$_3$, decamethylcyclopentasiloxane [(CH$_3$)$_2$SiO]$_5$, and the like is inevitable.

As methods for producing cyclic diorganosiloxanes having different compositions from the starting siloxanes, there have been known processes, for example, as disclosed in Japanese Pat. Appln. Kokoku (Post-Exam Publn) No. 2149/58 and Japanese Pat. Appln. Kokai (Laid-Open) No. 92025/74. These processes are favorable for producing trimers such as [(CH$_3$)$_2$SiO]$_3$ or the like, but not suitable for producing tetramers such as [(CH$_3$)$_2$SiO]$_4$ in high yields. The trimers have high reactivity and are useful compounds but have disadvantages in that, as general purpose starting materials for producing viscous siloxane oils and siloxane gums industrially, they are expensive in the production cost comparing with the tetramers and very difficult in handling due to their high melting points.

The present inventors have extensively studied industrial processes for producing [(CH$_3$)$_2$SiO]$_4$ effectively and found that, in a process for producing octamethylcyclotetrasiloxane by reacting dimethylsiloxane in a reactor in the presence of an inert solvent and an alkaline catalyst while distilling volatile cyclic dimethylsiloxanes and removing by-produced cyclic dimethylsiloxanes containing hexamethylcyclotrisiloxane from the volatile cyclic dimethylsiloxanes produced, higher convertion of the starting dimethylsiloxane to octamethylcyclotetrasiloxane can be obtained by recycling the separated by-produced cyclic dimethylsiloxanes containing at least hexamethylcyclotrisiloxane to the above-mentioned reactor. In other words, remarkable improvement can be attained in a process for producing octamethylcyclotetrasiloxane which comprises reacting dimethylsiloxane in the presence of an alkaline catalyst, an inert solvent and recycled by-produced cyclic dimethylsiloxanes containing at least hexamethylcyclotrisiloxane in a reactor, while distilling volatile cyclic dimethylsiloxanes produced, said recycled by-produced cyclic dimethylsiloxanes containing at least hexamethylcyclotrisiloxane having been separated from the volatile cyclic dimethylsiloxanes by recovering octamethylcyclotetrasiloxane and recycled to the reactor.

In the production of octamethylcyclotetrasiloxane by reacting dimethylsiloxane in a reactor in the presence of an inert solvent and an alkaline catalyst while distilling volatile cyclic dimethylsiloxanes, it is very difficult to lower the proportion of by-produced hexamethylcyclotrisiloxane to the extent of ignoring its amount by only selecting proper conditions in combination from the temperature, the pressure, kinds and amounts of catalysts, kinds and amounts of solvents, etc. Moreover, when an equilibrating reaction is conducted by the action of the alkaline catalyst as shown in Japanese Pat. Appln. Kokoku (Post-Exam Publn) No. 2149/58 and Japanese Pat. Appln. Kokai (Laid-Open) No. 92025/74, the reaction is rather oftenly led to a direction for favoring the production and distillation of hexamethylcyclotrisiloxane. In addition, the reaction is usually carried out under the conditions in which a temperature and a pressure is combined so that hexamethylcyclotrisiloxane is immediately vaporized. Nonetheless, the present inventors have unexpectedly found that the yield of octamethylcyclotetrasiloxane based on the starting dimethylsiloxane can surprisingly be improved comparing with the known processes by recycling by-produced cyclic dimethylsiloxanes containing at least hexamethylcyclotrisiloxane after recovering octamethylcyclotetrasiloxane from the volatile cyclic dimethysiloxanes distilled and accomplished the present invention based on the unexpected findings.

In accordance with the present invention, in a process for producing octamethylcyclotetrasiloxane comprising reacting dimethysiloxane in a reactor containing an inert solvent and an alkaline catalyst, distilling volatile cyclic dimethysiloxanes during the reaction, and separating by-produced cyclic dimethylsiloxanes containing at least hexamethylcyclotrisiloxane from the volatile cyclic dimethylsiloxanes to yield octamethylcyclotetrasiloxane, the improvement is obtained by recycling the separated by-produced cyclic dimethylsiloxanes containing at least hexamethylcyclotrisiloxane to the reactor.

Figure 2:
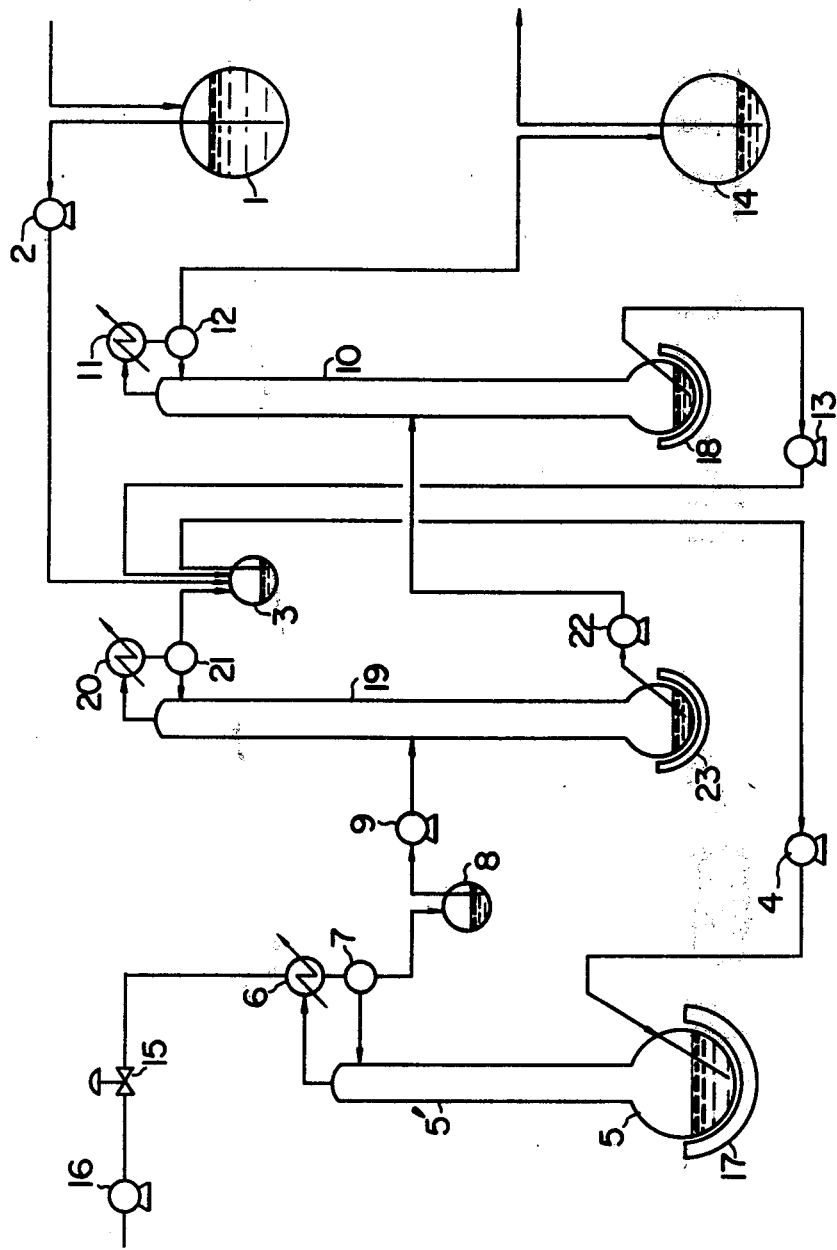
Figure 3:
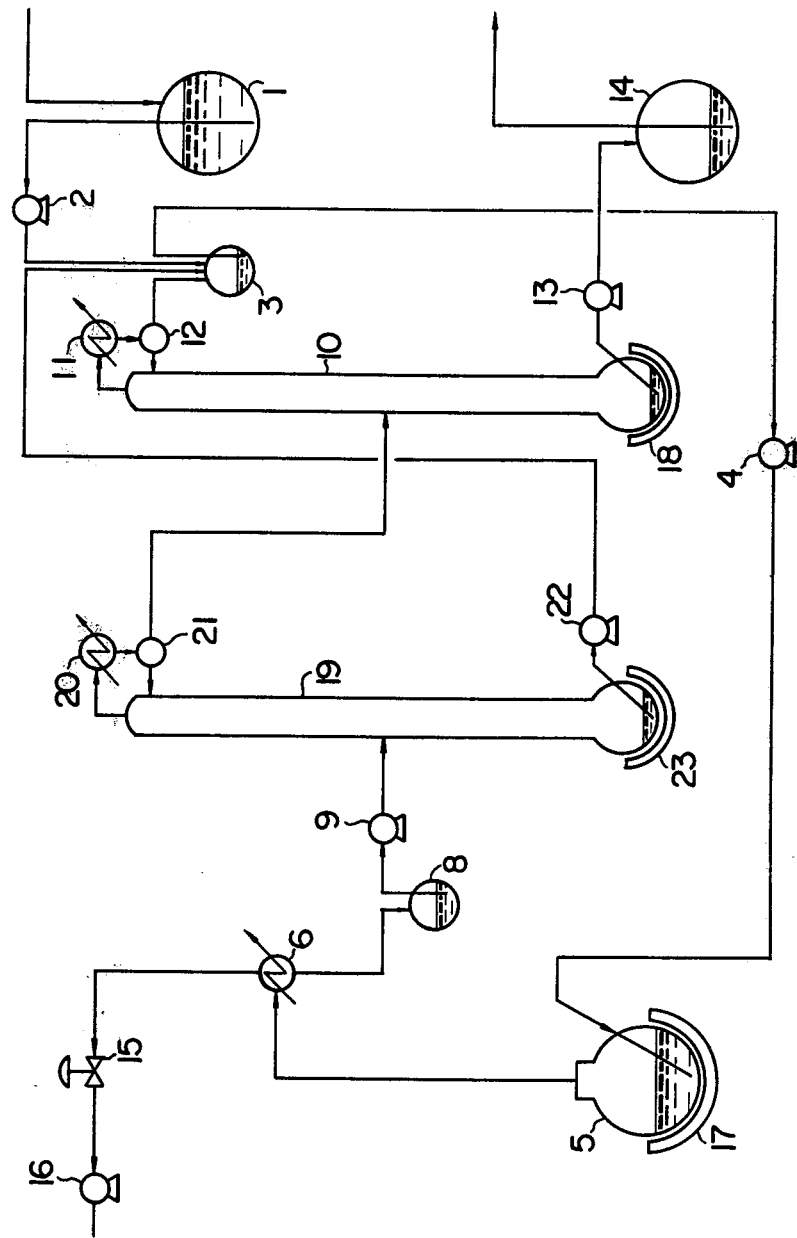

The attached drawings, FIGS. 1–3, are schematic flow diagrams showing preferred arrangements of apparatus elements and flow of materials therethrough suitable for practicing the present invention.

In the present invention, the term "volatile cyclic dimethylsiloxanes" is defined as a mixture of cyclic dimethylsiloxanes containing [(CH$_3$)$_2$SiO]$_3$ and [(CH$_3$)$_2$SiO]$_4$ as essential components and [(CH$_3$)$_2$SiO]$_n$ (n=5, 6, 7 and/or 8) as optional components and the term "by-produced cyclic dimethylsiloxanes" is defined as siloxanes constituting the volatile cyclic dimethylsiloxanes except for [(CH$_3$)$_2$SiO]$_4$ distilled from the reactor. Further, the volatile cyclic dimethylsiloxanes may contain small amounts of siloxanes other than the voltatile cyclic dimethyl siloxanes defined above as impurities; the desired product of the formula [(CH$_3$)$_2$SiO]$_4$ may contain the impurities included in the volatile cyclic dimethylsiloxanes and further by-produced cyclic dimethylsiloxanes depending on the degree of separation and by-produced cyclic dimethylsiloxanes may contain the impurities included in the volatile cyclic dimethylsiloxanes and further [(CH$_3$)$_2$Si- O]4 depending on the degree of separation, unless otherwise specified in the specification.

More in detail, the process of the present invention is characterized in that starting dimethylsiloxane is fed to a reactor containing an inert solvent and an alkaline catalyst, volatile cyclic dimethylsiloxanes are distilled off while conducting the reaction, [(CH$_3$)$_2$SiO]$_4$ is recovered from the volatile cyclic dimethylsiloxanes, and then among the residual by-produced cyclic dimethylsiloxanes, by-produced cyclic dimethylsiloxanes containing at least [(CH$_3$)$_2$SiO]$_3$ are recycled to the above-mentioned reactor in order to conduct the reaction together with starting dimethylsiloxane and/or its reaction product.

One example of methods for recycling the by-produced cyclic dimethylsiloxanes to the reactor is to remove [(CH$_3$)$_2$SiO]$_3$ and, if necessary, [(CH$_3$)$_2$SiO]$_n$ (n=5, 6, 7 and/or 8) from the volatile cyclic dimethylsiloxanes distilled from the reactor by distillation so as to purify [(CH$_3$)$_2$SiO]$_4$ and to feed the by-produced cyclic dimethylsiloxanes containing at least [(CH$_3$)$_2$SiO]$_3$ recovered by separation to the reactor again.

The starting dimethylsiloxane can be fed to the reactor intermittently, but a more preferable method is to feed the starting dimethylsiloxane to the reactor continuously. The by-produced cyclic dimethylsiloxanes can be recycled to the reactor intermittently, but a more preferable method is to recycle them continuously. A more preferred method can be carried out by feeding the starting dimethylsiloxane continuously to the reactor, separating the by-produced cyclic dimethylsiloxanes continuously from the volatile cyclic dimethylsiloxanes distilled, for example, by distillation for purifying [(CH$_3$)$_2$SiO]$_4$, and recycling continuously the by-produced cyclic dimethylsiloxanes separated to the reactor. The by-produced cyclic dimethylsiloxanes can be recycled to the reactor after storing them in an intermediate tank for a while.

The by-produced cyclic dimethylsiloxanes can be recycled to the reactor alone, but a preferable method is to recycle them to the reactor as a mixture with starting dimethylsiloxane. Further, the by-produced cyclic dimethylsiloxanes along or a mixture with starting dimethylsiloxane can be mixed with an inert solvent and an alkaline catalyst or a part of the reaction mixture in the reactor and can be fed to the reactor after prereacted.

The by-produced cyclic dimethylsiloxanes are obtained by separating them from the volatile cyclic dimethylsiloxanes distilled from the reactor, for example, by distillation and may contain a small proportion of [(CH$_3$)$_2$SiO]$_4$ depending on the degree of separation. But too large proportion of [(CH$_3$)$_2$SiO]$_4$ is not preferable, since not a small portion of the desired product [(CH$_3$)$_2$SiO]$_4$ is recycled to the reactor to be reacted again, which results in lowering in efficiency of the reactor. Therefore, the amount of [(CH$_3$)$_2$SiO]$_4$ in the recycling by-produced cyclic dimethylsiloxanes is controlled to preferably 0.20 part by weight or less, more preferably 0.06 part by weight or less, per part by weight of the recycling [(CH$_3$)$_2$SiO]$_3$ and preferably 0.15 part by weight or less, more preferably 0.05 part by weight or less, per part by weight of the recycling by-produced cyclic dimethylsiloxanes.

In the case of continuously feeding starting dimethylsiloxane and continuously recycling the by-produced cyclic dimethylsiloxanes to the reactor, the ratio of a recycling rate of the by-produced cyclic dimethylsiloxanes to a feeding rate of the starting dimethylsiloxane is preferably 0.02/1 to 1.2/1 on weight basis. If the ratio is less than 0.02/1, substantial effect of recycling the by-produced cyclic dimethylsiloxanes is lowered too much, while if the ratio is more than 1.2/1, the feeding rate of starting dimethylsiloxane to the reactor becomes too low, so that efficiency of the reactor is unfavorably lowered too much. A more preferable ratio is 0.06/1 to 0.6/1 on weight basis. Further, the ratio of a recycling rate of the by-produced cyclic dimethylsiloxanes to a distilling rate of the by-produced cyclic dimethylsiloxanes is preferably 0.2/1 to 3.0/1 on weight basis. If the ratio is less than 0.2/1, substantial effect of recycling the by-produced cyclic dimethylsiloxanes is lowered too much, while if the ratio is more than 3.0/1, the feeding rate of starting dimethylsiloxane to the reactor is lowered too much, so that efficiency of the reactor is unfavorably lowered. A more preferable ratio is 0.6/1 to 1.5/1 on weight basis. When the above-mentioned ratio is substantially 1/1 on weight basis, i.e. the distilled by-produced cyclic dimethylsiloxanes is recovered continuously and substantially the whole amount of the recovered by-produced cyclic dimethylsiloxanes is recycled to the reactor, a more preferable result can be obtained.

In the case of intermittently feeding or recycling either one of or both of starting dimethylsiloxane and the by-produced cyclic dimethylsiloxanes to the reactor, it is preferable to control the ratio of the average recycling rate to the average feeding rate and that of the average recycling rate to the average distilling rate within the above-mentioned ranges in the case of continuous feeding and recycling.

The reaction pressure is preferably in the range of $$0.03\ P_4 \leq P_r - P_s \leq 0.14\ P_4$$

more preferably in the range of $$0.05\ P_4 \leq P_r - P_s \leq 0.14\ P_4$$

wherein $P_r$ is the reaction pressure; $P_4$ is the vapor pressure of pure [(CH$_3$)$_2$SiO]$_4$ at the reaction temperature; and $P_s$ is the vapor pressure of the pure inert solvent at the reaction temperature. If the reaction pressure is too high, a distillation rate of the volatile cyclic dimethylsiloxanes from the reactor becomes unfavorably too slow, whereas if the reaction pressure is too low, a proportion of [(CH$_3$)$_2$SiO]$_3$ in the distilled volatile cyclic dimethylsiloxanes becomes too high and efficiency of the reactor is lowered. Further, with an increase of the proportion of [(CH$_3$)$_2$SiO]$_3$, when the volatile cyclic dimethylsiloxanes are condensed, the temperature at which crystals begin to deposit in the condensed solution becomes higher. In order to prevent the crystal deposition, it is necessary to select higher condensation temperature, which results in insufficient condensation of the distillate. On the other hand, if the condensation temperature is lowered below the temperature at which crystals begin to deposit, crystals deposit rapidly, which makes it very difficult to carry out the reaction while recycling the by-produced cyclic dimethylsiloxanes continuously. In any cases, pressures outside the above-mentioned range are not preferable from the viewpoint of industrial production.

In the process of the present invention, it is preferable to control a total siloxane concentration in the solvent in the reactor, that is, the proportion of the total weight of the compounds having siloxane linkages present in the solvent based on the weight of the reaction solution, within a suitable range. If the concentration is too low, a distillation rate of the volatile cyclic dimethylsiloxanes becomes unfavorably too slow, while if the concentration is too hight, it unfavorably becomes easily possible to bring about foaming due to an increased viscosity and decomposition of the siloxanes as well as generation of gelled materials. The lower limit of the concentration varies depending on the reaction temperature, the reaction pressure and the kind of solvent used, but a standard value can be given by the following equation:

$$\frac{100 (P_r - P_s) - P_4}{K P_4} \text{ (\% by weight)}$$

wherein $P_r$, $P_s$ and $P_4$ are as defined above; and K is 1.3 or less, preferably 0.8. The upper limit of the concentration is preferably 60% by weight, more preferably 40% by weight.

Dimethylsiloxane used as the starting material in the process of this invention means a polysiloxane having dimethylsiloxane groups $(CH_3)_2SiO_{1.0}$ as a constituent unit, or siloxane having linear, cyclic or crosslinked construction or construction in combination with two or more of them, containing as impurities constituent units of a small amount of trimethylsiloxane groups $(CH_3)_3SiO_{0.5}$ and/or monomethylsiloxane groups $CH_3SiO_{1.5}$ and/or hydroxy groups, etc. other than dimethylsiloxane groups, or a mixture of them.

The proportion of the dimethylsiloxane group in the starting dimethylsiloxane is preferably 90% by weight or more, more preferably 98% by weight or more. A preferable example of the starting dimethylsiloxane is, for example, a hydrolyzate of industrial dimethyldichlorosilane. A low molecular weight polydimethylsiloxane recovered from the production process of high molecular weight polydimethylsiloxanes can also be used as the starting dimethylsiloxane alone or more preferably in combination with the hydrolyzate of industrial dimethyldichlorosilane.

The inert solvent used in the process of the present invention is an organic compound which is liquid at the reaction temperature and dissolves completely or almost dimethylsiloxane reaction products at the reaction temperature and does not react with the starting material, the catalyst and the reaction products.

Examples of the inert solvents are aryl alkyl hydrocarbons, dialkyl ethers, diaryl ethers, aryl alkyl ethers, aryl hydrocarbons, aryl alkyl hydrocarbons, partially hydrogenated aryl hydrocarbons, and linear or cyclic alkyl hydrocarbons. These organic compounds can be used alone or as a mixture of two or more of them. Preferable examples of the insert solvents are aryl hydrocarbons having 10 or more carbon atoms, dialkyl ethers having 10 or more carbon atoms, aryl alkyl ethers having 10 or more carbon atoms, partially hydrogenated aryl hydrocarbons having 10 or more carbon atoms, alkyl hydrocarbons having 11 or more carbon atoms, aryl alkyl hydrocarbons having 11 or more carbon atoms, and diaryl ethers having 11 or more carbon atoms, all of these compounds having a boiling point of preferably 185° C. or more, more preferably 200° C. or more and having a melting point of preferably 100° C. or less, more preferably 75° C. or less. Concrete examples of these compounds are biphenyl, dihexyl ether, tetralin, octadecane, diphenyl ethane, diphenyl ether, etc. Most preferable examples of the inert solvents are diphenyl ether, biphenyl and a mixture of them.

As the alkaline catalyst, there can be used alkali metals and their alkaline compounds. Alkaline compounds useful as catalyst include hydroxides, oxides, carbonates and bicarbonates of alkali metals such as potassium, caesium, etc., and dimethyl silanolates of alkali metals, etc. These compounds can be used alone or as a mixture of two or more of them. Particularly preferable examples of the catalyst are potassium hydroxide and/or potasium dimethylsilanolate.

The alkali metal or its alkaline compound as catalyst is used in a concentration of 0.0005 to 0.1 part by weight, preferably 0.001 to 0.02 part by weight, as the alkali metal, per part by weight of the solvent. The alkali metal or its alkaline compond should be used as catalyst by adjusting it so as to offset the presence of anions such as chlorine ions, and the like.

The reaction temperature employed in the process of the present invention is preferably 120° to 200° C., more preferably 140° to 180° C.

As the reactor used in the process of the present invention, there can be used a reactor having an opening for evaporation, or a reactor having an opening for evaporation and a fractional distillation column the bottom of which is directly connected to the opening designed so as to decrease the contents of higher boiling point components in the distilled volatile cyclic dimethylsiloxanes.

The present invention is illustrated more in detail referring to the attached drawings.

FIG. 1 is a schematic flow diagram showing arrangement of apparatus elements and flow of materials therethrough suitable for practicing the present invention. In FIG. 1, numeral 1 denotes a tank for storing starting dimethylsiloxane, numeral 2 denotes a pump, numeral 3 denotes a receiver for mixing the starting dimethylsiloxane with a distillate from the column head of a rectifying column described hereinafter, numeral 4 denotes a pump, numeral 5 denotes a reactor having an opening for evaporation and a fractional distillation column (5') directly connected to the opening for evaporation, numeral 6 denotes a condenser, numeral 7 denotes a fractional distillation head for controlling the reflux ratio, numeral 8 denotes a receiver, numeral 9 denotes a pump, numeral 10 denotes a rectifying column having a feed opening in the middle, numeral 11 denotes a condenser, numeral 12 denotes a fractional distillation head for controlling the reflux ratio, numeral 13 denotes a pump, numeral 14 denotes a receiver, numeral 15 denotes a valve for adjusting degree of vacuum so as to control the pressures of the reactor 5, the fractional distillation column 5', the condenser 6 and the receiver 8 at appropriate reduced pressure, numeral 16 denotes a vacuum pump, numeral 17 denotes a heater for heating the reactor 5 and numeral 18 denotes a heater for heating the bottom of the rectifying column 10.

The process of the present invention can be practiced by using the above-mentioned apparatus elements as follows. A hydrolyzate of industrial dimethyldichlorosilane stored in the starting dimethylsiloxane storing tank 1 is passed to the receiver 3 by the action of the pump 2. The siloxane stored in the receiver 3 is passed to the reactor 5 containing a mixture of diphenyl ether as a solvent and potassium hydroxide as a catalyst by the action of the pump 4. The reactor 5 is heated by the heater 17 and maintained under reduced pressure by using the vacuum pump 16 and the valve 15 for adjusting degree of vacuum. Volatile cyclic dimethylsiloxanes evaporated from the reactor 5 undergoes fractional distillation in the fractional distillation column 5' directly connected to the opening for evaporation, and cyclic dimethylsiloxanes containing [(CH$_3$)$_2$SiO]$_3$ and [(CH$_3$)$_2$SiO]$_4$ as main components are distilled out and stored in the receiver 8. On the other hand, cyclic dimethylsiloxanes rich in higher boiling point components are refluxed to the reactor 5 from the fractional distillation column 5'. The siloxanes stored in the receiver 8 is fed to the rectifying column 10 by the action of the pump 9. The rectifying column 10 is operated by the conventional method and cyclic dimethylsiloxanes rich in [(CH$_3$)$_2$SiO]$_3$ are distilled out from the head of the column and passed to the receiver 3 through the condenser 11 and the fractional distillation head 12. In the receiver 3, the cyclic dimethylsiloxanes rich in [(CH$_3$)$_2$SiO]$_3$ are mixed with the hydrolyzate of industrial dimethyldichlorosilane which is the starting material and the cyclic dimethylsiloxanes rich in [(CH$_3$)$_2$SiO]$_3$ are recycled to the reactor 5 as a mixture with the starting material by the action of pump 4. On the other hand, cyclic dimethylsiloxanes rich in [(CH$_3$)$_2$SiO]$_4$ flowed down to the bottom of the column is passed to the receiver 14 by the action of the pump 13.

The above-mentioned process is only one example of the process of the present invention, which is not limited to it. The process of the present invention can be practiced in other manners such as shown in FIGS. 2 and 3.

The process shown in FIG. 2 further comprises, in addition to the process of FIG. 1, purifying the cyclic dimethylsiloxanes rich in [(CH$_3$)$_2$SiO]$_4$ in another rectifying column to remove higher boiling point materials such as [(CH$_3$)$_2$SiO]$_5$, passing the removed higher boiling point materials such as [(CH$_3$)$_2$SiO]$_5$ to the receiver 3, and recycling them to the reactor 5. In FIG. 2, numerals 1–18 denote the same elements as defined in FIG. 1, and numeral 19 denotes a rectifying column, numeral 20 denotes a condenser, numeral 21 denotes a fractional distillation head, numeral 22 denotes a pump and numeral 23 denotes a heater.

The process shown in FIG. 3 is changed from that shown in FIG. 1 in the following points. The reactor 5 having the opening for evaporation and the fractional distillation column directly connected to the opening for evaporation as shown in FIG. 1 is replaced by a reactor having an opening for evaporation. Volatile cyclic dimethylsiloxanes distilled from the reactor is condensed and passed to the newly installed rectifying column 19, wherein [(CH$_3$)$_2$SiO]$_n$ (n=5, 6, 7 and/or 8) is separated to the desired degree and the purified portions are passed to the rectifying column 10. The separated [(CH$_3$)$_2$SiO]$_n$ (n=5, 6, 7 and/or 8) is recycled to the reactor 5 through the receiver 3. In FIG. 3, the numerals show the same elements as defined in FIG. 2. The process of FIG. 3 as well as that of FIG. 2 is a preferable embodiment of the present invention.

In the processes of FIGS. 2 and 3, the starting dimethylsiloxane is continuously fed to the reactor and the by-product cyclic dimethylsiloxanes distilled are continuously recovered and substantially the whole amounts thereof are recycled to the reactor continuously, that is the ratio of recycling rate of the by-produced cyclic dimethylsiloxanes to distilling rate of the by-produced cyclic dimethylsiloxanes is substantially 1 on the weight basis, which are the most preferable examples of the process of the present invention.

The fractional distillation column and the rectifying columns mentioned above can be designed depending on the composition of the volatile cyclic dimethylsiloxanes, the composition of the by-produced cyclic dimethylsiloxanes, the purity of the desired product of [(CH$_3$)$_2$SiO]$_4$, and the kinds and concentrations of impurities included in these compounds mentioned above.

The present invention is illustrated by way of the following examples in which all percents are by weight unless otherwise specified. The terms used in the following examples are defined as follows:

$$\text{Recovery percent of dimethylsiloxanes} = \frac{\text{Weight of recovered dimethylsiloxanes}}{\text{Weight of starting dimethylsiloxane fed}} \times 100 \, (\%)$$

The term "recovered dimethylsiloxanes" means in Comparative Example 1 the volatile cyclic dimethylsiloxane distilled out from the head of the fractional distillation column attached to the reactor, and in Examples 1 to 3 the bottoms taken out of the bottom of the rectifying column.

$$\text{Yield of } [(CH_3)_2SiO]_4 = \left(\begin{array}{c}\text{Recovery}\\\text{percent of}\\\text{dimethyl-}\\\text{siloxanes}\end{array}\right) \times \left(\begin{array}{c}\text{Content of } [(CH_3)_2SiO]_4\\\text{the recorered}\\\text{dimethylsiloxanes}\end{array}\right) (\%)$$

$$\text{Recycle ratio} = \frac{\text{Recycle rate of the by-produced cyclic dimethylsiloxanes}}{\text{Feeding rate of starting dimethylsiloxane}}$$

COMPARATIVE EXAMPLE 1

In a reactor, 1 liter of a 30% HCl aqueous solution was placed and stirred vigorously. To the HCl solution, dimethyldichlorosilane containing 0.3% of methyltrichlorosilane CH$_3$SiCl$_3$ and 0.2% of trimethylchlorosilane (CH$_3$)$_3$SiCl was fed at a constant rate of 5.6 g/min and simultaneously water was fed to the reactor at a rate so as to maintain the concentration of HCl in the HCl aqueous solution at 30%. Hydrolysis of dimethyldichlorosilane was conducted at 0° C. After the reaction, the reaction mixture was allowed to stand so as to form two layers. The upper oil layer was separated and mixed with an equal amount of water and shaked sufficiently. Subsequently, the oil layer was separated again and the water dispersed in the oil layer was removed by centrifugation to give a transparent oil (starting dimethylsiloxane (I)).

In a reactor equipped with a fractional distillation column, 20 g of the starting dimethylsiloxane (I), 0.1 g of a 50% KOH aqueous solution and 50 g of diphenyl ether were placed. The mixture was heated to 158° C. under a pressure of 80 mm Hg. When a liquid began to distil from the head of the fractional distillation column, the starting dimethylsiloxane (I) was fed to the reactor at a rate of 0.8 g/min through a glass pipe inserted under the liquid level of the reaction mixture and the temperature of a heating bath of the reactor was controlled so as to make the distilling rate about 0.8 g/min. After the feeding rate of the starting dimethylsiloxane (I) was almost balanced to the distilling rate of the distillate from the head of the fractional distillation column (distillate (I)), 240.5 g of the starting dimethylsiloxane (I) was fed to the reactor and 235.0 g of the distillate (I) was collected in a receiver in 5 hours. During the above-mentioned period, the reaction temperature was maintained at 159°-160° C. and the reaction pressure was maintained at 80-82 mm Hg.

Table 1 shows the results of analysis of the starting dimethylsiloxane (I) and the distillate (I). The yield of $[(CH_3)_2SiO]_4$ based on the starting dimethylsiloxane fed was 74.7%.

Table 1

| Component | Starting dimethyl-siloxane (I) (%) | Distillate (I) (%) |
| --- | --- | --- |
| $[(CH_3)_2SiO]_3$ | 0.05 | 21.03 |
| $[(CH_3)_2SiO]_4$ | 56.33 | 76.40 |
| $[(CH_3)_2SiO]_5$ | 9.96 | 2.50 |
| Other siloxanes | 33.66 | 0.07 |

EXAMPLE 1

Apparatus elements and a flow sheet as shown in FIG. 1 were used. In the reactor 5, 100 g of diphenyl ether and 2.0 g of a 50% KOH aqueous solution were placed. A hydrolyzate of dimethyldichlorosilane prepared by the same method as described in Comparative Example 1 (starting dimethylsiloxane (II)) was fed to the reactor 5 at a rate of 1.46 g/min from the starting dimethylsiloxane storing tank 1 through the receiver 3 by the action of the pump 2 and pump 4. The reaction was carried out at 160° C. and 110 mm Hg and the distillate was fractionated in the fractional distillation column 5' at a reflux ratio of about 5 and the distillate was collected in the receiver 8. To the condenser 6, cooling water at 19° C. was supplied. The distillate stored in the receiver 8 was passed to the rectifying column 10 by the action of pump 9 so as to maintain the liquid level of the receiver 8 at a constant height. The rectifying column was operated according to a conventional method. The distillate from the rectifying column enriched in $[(CH_3)_2SiO]_3$ was passed to the receiver 3 and mixed with the starting dimethylsiloxane (II) so that the distillate was dissolved in the latter. The cyclic dimethylsiloxanes enriched in $[(CH_3)_2SiO]_3$ were recycled to the reactor 5 as a mixture with the starting dimethylsiloxane by the action of the pump 4. The liquid level of the receiver 3 was controlled by the action of the pump 4 to maintain a constant level. The bottoms enriched in $[(CH_3)_2SiO]_4$ (recovered dimethylsiloxanes (I)) stored at the bottom of the rectifying column was taken out at a rate of 1.41 g/min by the action of the pump 13 after 2 hours from the beginning of the reaction and collected in the receiver 14. The reaction was conducted for 42 hours after the steady state was reached. During said Period, 3677 g of the starting dimethylsiloxane (II) was fed to the reactor and 3548 g of the bottoms (recovered dimethylsiloxane (I)) were obtained. During said period, the average delivery rate of the pump 4 was 1.77 g/min and that of the pump 9 was 1.71 g/min and the concentration of the total siloxanes in the reaction mixture in the reactor was about 26%.

Table 2 shows the results of analysis of the the starting dimethylsiloxane (II), the distillate from the reactor sampled at the exit of the pump 9 (distillate (II)) and the recovered dimethyl siloxanes (I). Other results are as follows:

| | |
| --- | --- |
| Recovery percent of dimethylsiloxanes: | 96.5% |
| Yield of $[(CH_3)_2SiO]_4$: | 95.9% |
| Recycle ratio: | 0.22 |

As is clear from the above results, the yield of $[(CH_3)_2SiO]_4$ is by far superior to that of Comparative Example 1, i.e. 74.7%, wherein the by-produced cyclic dimethylsiloxanes containing $[(CH_3)_2SiO]_3$ was not recycled.

Table 2

| Component | Starting dimethyl-siloxane (II) (%) | Distillate (II) (%) | Recovered di-methylsiloxanes (I) (%) |
| --- | --- | --- | --- |
| $[(CH_3)_2SiO]_3$ | 0.05 | 18.32 | 0.13 |
| $[(CH_3)_2SiO]_4$ | 55.93 | 81.31 | 99.42 |
| $[(CH_3)_2SiO]_5$ | 8.46 | 0.33 | 0.40 |
| Other siloxanes | 35.56 | 0.04 | 0.05 |

EXAMPLES 2 AND 3

Using the same procedures as described in Example 1, the starting dimethylsiloxane was prepared and $[(CH_3)_2SiO]_4$ was produced therefrom.

Table 3 shows the reaction conditions employed and the results obtained therefrom. In each Example, the yield of $[(CH_3)_2SiO]_4$ was superior to that of Comparative Example 1.

Table 3

| | Example 2 | Example 3 |
| --- | --- | --- |
| Reaction conditions | | |
| Reaction temperature | 160° C. | 160° C. |
| Reaction pressure | 80 mm Hg | 70 mm Hg |
| Temp. of cooling water supplied to condenser 6 | 25° C. | 35° C. |
| Amount of diphenyl ether fed to the reactor | 50 g | 40 g |
| Amount of 50% KOH soln. fed to the reactor | 0.51 g | 0.38 g |
| Feeding rate of starting dimethylsiloxane | 1.59 g/min | 0.86 g/min |
| Recycle ratio | 0.34 | 0.50 |
| Recovery of | | |

Table 3-continued

|  | Example 2 | Example 3 |
| --- | --- | --- |
| dimethyl-siloxanes | 92.4% | 87.1% |

| Composition of siloxanes (%) | Starting dimethyl-siloxane | Distillate from the reactor | Recovered dimethyl-siloxanes | Starting dimethyl-siloxane | Distillate from the reactor | Recovered dimethyl-siloxanes |
| --- | --- | --- | --- | --- | --- | --- |
| $[(CH_3)_2SiO]_3$ | 0.09 | 26.45 | 0.07 | 0.09 | 36.04 | 0.15 |
| $[(CH_3)_2SiO]_4$ | 55.59 | 72.98 | 99.15 | 55.59 | 63.12 | 98.80 |
| $[(CH_3)_2SiO]_5$ | 8.40 | 0.49 | 0.68 | 8.40 | 0.71 | 0.94 |
| Other siloxanes | 35.92 | 0.08 | 0.10 | 35.92 | 0.13 | 0.11 |
| Yield of $[(CH_3)_2SiO]_4$ |  | 91.6% |  |  | 86.1% |  |

What is claimed is:

1. In a process for producing octamethylcyclotetrasiloxane comprising reacting dimethylsiloxane in a reactor containing an inert solvent and an alkaline catalyst, distilling volatile cyclic dimethylsiloxanes during the reaction, and separating by-produced cyclic dimethylsiloxanes containing at least hexamethylcyclotrisiloxane from the volatile cyclic dimethylsiloxanes to yield octamethylcyclotetrasiloxane, the improvement which comprises recycling the separated by-produced cyclic dimethysiloxanes containing at least hexamethylcyclotrisiloxane to the reactor.

2. A process according to claim 1, wherein the reactor has an opening for evaporation and a fractional distillation column the bottom of which is directly connected to the opening for evaporation.

3. A process according to claim 1, wherein the reaction is carried out under a pressure in the range of $$0.03P_4 \leq P_r - P_s \leq 0.14P_4$$

wherein $P_r$ is the reaction pressure; $P_4$ is the vapor pressure of pure octamethylcyclotetrasiloxane at the reaction temperature; and $P_s$ is the vapor pressure of the pure inert solvent at the reaction temperature.

4. A process according to claim 1, wherein the reaction is carried out in a total siloxane concentration in the reaction solution ranging from the upper limit of 60% by weight to the lower limit of $$\frac{100(P_r - P_s) - P_4}{1.3 P_4} \text{ \% by weight}$$

wherein $P_r$ is the reaction pressure; $P_4$ is the vapor pressure of pure octamethylcyclotetrasiloxane at the reaction temperature; and $P_s$ is the vapor pressure of the pure inert solvent at the reaction temperature.

5. A process according to claim 1, wherein the by-produced cyclic dimethylsiloxanes are separated from the volatile cyclic dimethylsiloxanes distilled form the reactor by distillation.

6. A process according to claim 1, wherein the insert solvent is an aryl hydrocarbon having 10 or more carbon atoms, a dialkyl ether having 10 or more carbon atoms, an aryl alkyl ether having 10 or more carbon atoms, a partially hydrogenerated aryl hydrocarbon having 10 or more carbon atoms, an alkyl hydrocarbon having 11 or more carbon atoms, an aryl alkyl hydrocarbon having 11 or more carbon atoms, or a diaryl ether having 11 or more carbon atoms, or a mixture of two or more of them, said inert solvent having a boiling point of 185° C. or more and a melting point of 100° C. or less.

7. A process according to claim 1 or 6, wherein the inert solvent is diphenyl ether and/or biphenyl.

8. A process according to claim 1, wherein the alkaline catalyst is an alkaline compound of potassium.

9. A process according to claim 8, wherein the alkaline compound of potassium is potassium hydroxide and/or potassium dimethylsilanolate.

10. A process according to claim 1, wherein the reaction is carried out at a temperature of 120° C. to 200° C.

11. A process according to claim 1, wherein the starting dimethylsiloxane is a hydrolyzate of industrial dimethyldichlorosilane.

12. A process according to claim 1, wherein the starting dimethylsiloxane is a low molecular weight polydimethylsiloxane recovered from a production process of high molecular weight polydimethylsiloxanes, or a mixture of the low molecular weight polydimethylsiloxane and a hydrolyzate of industrial dimethyldichlorosilane.

13. A process according to claim 1, wherein the starting dimethylsiloxane is fed to the reactor continuously and the by-produced cyclic dimethylsiloxanes are recycled to the reactor continuously, the ratio of a recycling rate of the by-produced cyclic dimethylsiloxanes to a feeding rate of the starting dimethylsiloxane being 0.02/1 to 1.2/1 on weight basis.

14. A process according to claim 1 or 5, wherein a ratio of a recycling rate of the by-produced cyclic dimethylsiloxanes to a distilling rate of the by-produced cyclic dimethylsiloxanes is 0.2/1 to 3.0/1 on weight basis.

* * * * *